United States Patent [19]

Collins

[11] 4,399,713

[45] Aug. 23, 1983

[54] DEVICE FOR SAMPLING MOLTEN MATERIAL AND MEANS FOR OPERATING SAME

[76] Inventor: William J. Collins, 7005 Madison St., Merrillville, Ind. 46410

[21] Appl. No.: 277,198

[22] Filed: Jun. 25, 1981

[51] Int. Cl.³ ............................................. G01N 1/12
[52] U.S. Cl. ............................. 73/864.54; 73/864.56; 73/864.59
[58] Field of Search ........... 73/863.31, 864.53, 864.59, 73/864.73

[56] References Cited

U.S. PATENT DOCUMENTS

| | | | |
|---|---|---|---|
| 2,608,303 | 8/1952 | Ford | 73/864.73 |
| 3,656,338 | 4/1972 | Collins | 73/863.31 |
| 3,798,974 | 3/1974 | Boron | 73/DIG. 9 |
| 4,002,072 | 1/1977 | Collins | 73/864.56 |
| 4,068,530 | 1/1978 | Collins | 83/864.57 |
| 4,211,117 | 7/1980 | Cure | 73/DIG. 9 |
| 4,213,342 | 7/1980 | Gates | 73/864.61 |

Primary Examiner—S. Clement Swisher
Attorney, Agent, or Firm—Charles S. Penfold

[57] ABSTRACT

The subject invention involves a device which may be referred to as a sampler for obtaining a sample of molten material from a supply thereof and an aspirator apparatus or air pressure system which is adapted for detachable operative connection with the device in a manner to provide a vacuum whereby to induce, promote or cause the molten material to expeditiously flow into and substantially completely fill a chamber or chambers constituting the receiving means of the device to obtain a well formed sample or samples for analysis.

27 Claims, 17 Drawing Figures

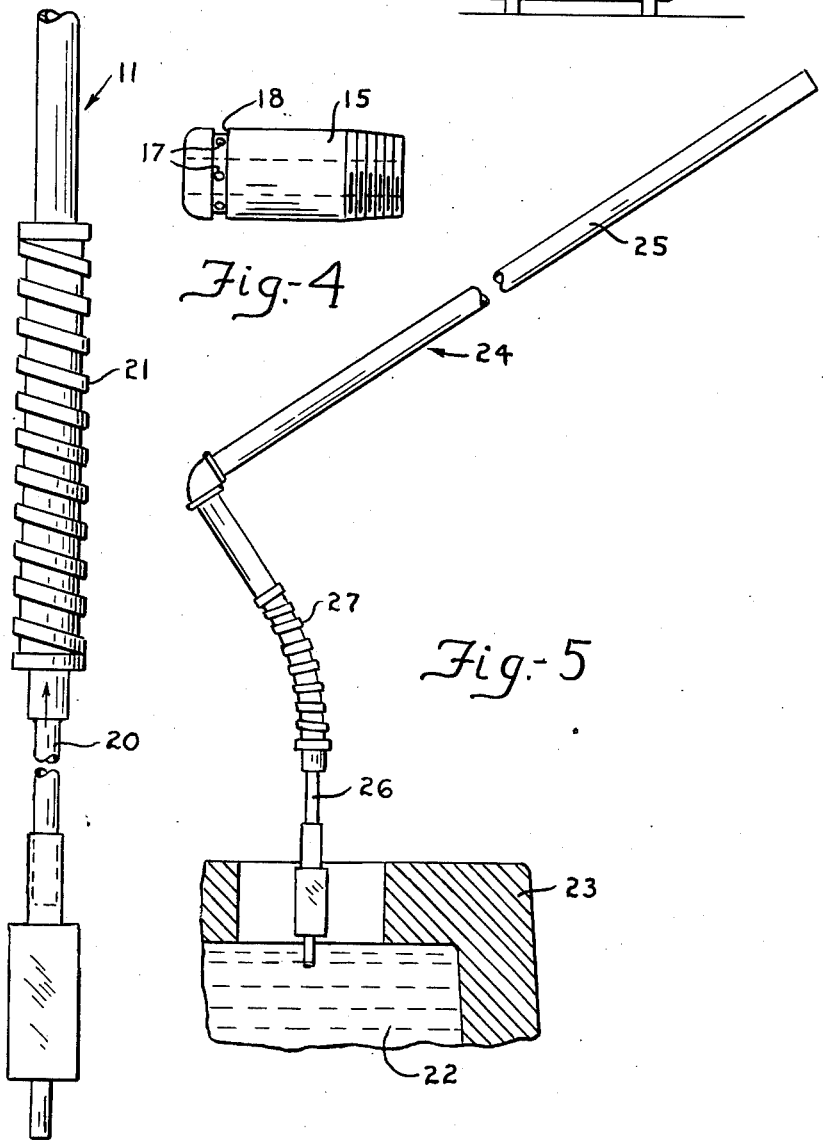

DEVICE FOR SAMPLING MOLTEN MATERIAL AND MEANS FOR OPERATING SAME

BACKGROUND OF THE INVENTION

It is recognized that many various forms or types of devices have heretofore been employed and are presently being utilized for the purpose of obtaining samples of molten material or metal from a supply thereof.

It is also recognized that many Patents have issued which are directed to sampling devices which are constructed for connection to a vacuum or air pressure system which is located remote from such devices. Certain of such Patents, for example, include Heinrich Feichtinger U.S. Pat. No. 2,970,350; Tilbert Cavalier U.S. Pat. Nos. 3,255,634 and 3,309,928; James R. Judge et al U.S. Pat. No. 3,915,014; and Van L. Vierbicky U.S. Pat. No. 4,125,024. Furthermore other Patents disclose the use of means contained in or constituting an integral component of a device whereby a vacuum may be created to induce flow of a sample of such a material into a device and these include, for example, those of Richard A. Falk U.S. Pat. Nos. 3,791,220; 3,905,238; and 3,996,803 and Edward A. Kelsey U.S. Pat. No. 4,007,641.

OBJECTIVES

Consideration of the systems and devices disclosed in the Patents above referred to, may possess certain advantages but none appear to disclose the attributes or objectives of the subject invention as set forth hereinafter:

More particularly, an important objective of the subject invention is to provide a device for obtaining a sample of molten material which embodies improved principles of design and construction whereby it can be readily detachably operatively connected to an air pressure system and a component of the latter constitutes a lance for manipulating the device for entry into a supply of such a material.

A significant object of the invention is to provide an assembly which can be readily operatively connected to an air pressure system in a manner whereby the assembly can utilize or convert that system to promote the flow of a sample of molten material into a sampler device.

The assembly referred to in the preceding paragraph is considered to constitute a unique and meritorious advance in the art and includes a tubular lance comprising a rear extremity and a front extremity which is connected to the rear extremity by what may be termed a flexible or universal joint or a connection means which allows an operator, for example, to manually move the outer extremity and a sampler device adapted to be carried thereby relative to the rear extremity. This manually movable or manueverability factor permits an operator to readily position a sampler or device at any desired location for entry into a supply of molten material, without requiring the operator to change his stance or position relative to the supply.

An important object of the invention is to provide a device or sampler which embodies improved principles of design and instruction and comprises, among other things, wall structure which forms a generally centrally disposed receiving means or chamber; a front entrance tube or tubular means preferably constructed of a non-metallic material, such as, for example, quartz or Pyrex, which tube is communicatively connected to the chamber; a sleeve or tubular member which supports and protects the entrance or inlet tube; a rear outlet tube or tubular means, also preferably constructed of quartz or Pyrex which is communicatively connected to the chamber; and a plurality of telescopically connected sleeves or members which surround, protect or support the outlet tube and provide a socket or seat to sealably accommodate a tubular front extremity of a lance for detachably connecting the device thereto.

A specific, but important object is to provide a lance, independent of a pressure system which has a universal joint or flexible connection means intermediate its length whereby a device connected to the lance can be manipulated in substantially any direction desired, thereby facilitating entry of the device into a supply of molten material.

A further specific object is to design and construct a lance of the character described in the preceding paragraph so that it is of a sufficient length and weight whereby to additionally assist and promote convenient manipulation when, for example, the physical ability of an operator may be below average.

A further object of the invention is to provide a wall structure which forms a chamber and an opening and a tubular means which is resiliently supported in the opening for communication with the chamber.

Another specific object is to provide a pluurality of different elements or fittings, any one of which can be utilized in the air pressure structure or system to promote evacuation of air in a lance and a sampler attached to the latter.

Additional objects and advantages of the invention or inventions will become apparent after the description hereinafter set forth is considered in conjunction with the drawings annexed hereto.

DRAWINGS

In the drawings:

FIG. 1 depicts an air pressure system including a lance operatively connected thereto for detachably supporting a device for obtaining a sample of molten material from a supply thereof;

FIGS. 2, 3 and 4 disclose various elements any one of which can be utilized in the system whereby to assist in converting the air pressure in the system to create a vacuum in a lance and thereby cause such a material to be sucked into the device;

FIG. 5 is an elevational view of a lance structure which can be employed without utilizing an air pressure or vacuum system;

DESCRIPTION

Figure 6:
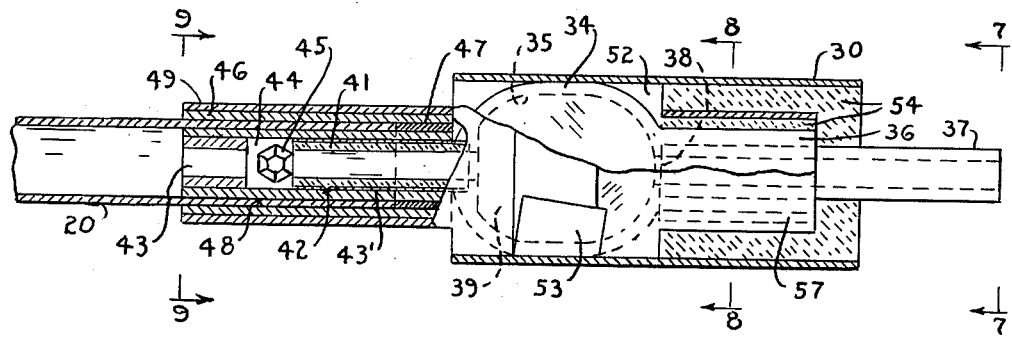
FIG. 6 is a longitudinal sectional view of a device or sampler which can be employed as in FIG. 1.
Figure 9:
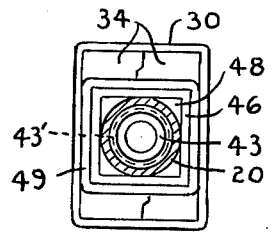
FIG. 9 is a rear end view of the device looking in the direction of the arrows 9—9 of FIG. 6.

Referring to FIG. 1, there is illustrated an aspirator apparatus, air pressure system or structure generally designated 1 comprising a convention pump, tank and power unit and an assembly generally designated 2 which is detachably operatively connected by a flexible hose 3 to a fitting 4 extending from a manually operable valve 5 and to a fitting 6 carried by piping 7 extending from the tank of the structure.

The assembly 2 may be designed and constructed in various ways but preferably includes a tubular member or length of pipe 8, one end of which is connected to the valve 5 and its opposite end to a coupling in the form of a T-shaped pipe fitting 9. The assembly also includes a tubular member or length of pipe 10 connected to the fitting 9 in an axial spaced relationship to the pipe 8 and a tubular member or length of piping which is connected to the fitting 9 and serves to constitute a lance assembly generally designated 11. The end of the pipe 8 in the fitting 9 is preferably internally threaded whereby an externally threaded portion of an element 12, shown in FIG. 3, can be readily detachably connected to the pipe 8, the arrangement being such that when air under pressure, for example, within a range of between 90 and 125 P.S.I. is caused to flow through the piping 7, hose 3, valve 5, pipe 8 and through a reduced opening 13 in the element 12 a jet of air under increased pressure will flow through the fitting 9 and pipe 10 to cause any air in the lance 11 to be sucked out of the lance or create a vacuum therein, as indicated by the flow pattern of the arrows, for the purpose promoting or expediting the flow of a hot liquid, such as a molten material into a device, such as those illustrated in FIGS. 6, 12, 13 and 14 for obtaining a sample of such a material for analysis.

It is to be understood that when a gauge connected to the tank of the pressure system shows that a sufficient pressure has been obtained to produce the desired suction or vacuum in the lance, the valve 5 is manually opened to allow the air pressure to perform its intended function. A spring, now shown, serves to return the valve, which is of a conventional character, to a closed position. It is to be further understood, that the assembly 2 can be attached to any conventional air pressure system or aspirator apparatus, for example, one that has already been installed in relative close proximity to a location where the sample is to be obtained and may be used for other purposes. Moreover, if so desired the lance 11 can be directly operatively connected to a suction line, without utilizing the assembly 2 or it can be employed as depicted in FIG. 5 to the exclusion of a vacuum or air pressure system as will be described subsequently.

As alluded to above, FIGS. 2 and 4 disclose tubular elements or fittings and these are respectively identified as 14 and 15. Either of these may be employed as a substitute for the element 12 described above. The element 14 has a tapered front extremity or nose generally like the nose of the element 12 and is provided with a plurality of jet openings or apertures 16, in lieu of the single opening 13 in the element 12. The element 15 is provided with an axial passage like the elements 12 and 14 and with a plurality of circumferentially spaced radially extending jet openings 17 which are communicatively connected to the axial passage and terminate outwardly into a circumferential groove 18, all of which serves to provide tubulance and suction in the lance 11.

The lance assembly 11 may be designed and constructed in various ways and as depicted preferably comprises an inner tubulaar member, pipe section or rear extremity 19 and an outer tubular member, pipe section or front extremity 20, the latter of which serves to detachably support a device, for example, of the character shown in FIGS. 6, 12, 13 and 14 as alluded to above. More specifically, the rear and front extremities of the lance are preferably attached by a connecting means 21 which offers a setup whereby the outer extremity and a device carried thereby can be readily manipulated as a unit relative to the inner extremity in a manner whereby to facilitate insertion of an entrance tube of the device into a supply of molten material 22 contained in a vessel 23 such as is disclosed in FIG. 5.

Referring to FIG. 5 there is shown a lance assembly generally designated 24 which can be employed without utilizing an air pressure or vacuum system or necessarily a device, such as is described in FIGS. 6, 12, 13 and 14. Otherwise expressed the lance can be employed to support various forms of devices for obtaining samples of molten material from a vessel or flowing stream.

More particularly, the lance assembly 24 preferably comprises an inner elongated extremity 25 having an offset and a front relatively short front extremity 26 which is preferably attached to the offset or inner extremity by a connecting means 27 which offers a setup whereby the front extremity and a device or sampler carried thereby can be flexibly or substantially universally adjusted for relative movement in order that an operator can better position the device for use in obtaining a sample from the supply 22. The lance 24 is tubular and relatively light in weight to promote ease in handling and the same is substantially true of the lance 11 even though the latter is attached to the fitting 9. The inner extremity 25 constitutes a handle and if so desired the connecting means 27 can be directly connected to the handle without utilizing the offset thereof.

The lance 11 is preferably employed to support devices of the character depicted in FIGS. 6, 12, 13 and 14 because these devices are designed and constructed that they are responsive to the suction created in the lance to expedite or induce the flow of a sample of molten material into a chamber or chambers of the devices to completely fill the same with the material to obtain well shaped sample portions for analysis.

Figure 8:
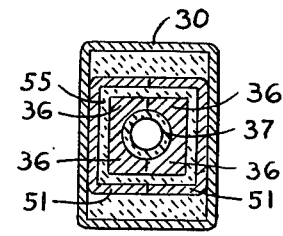
FIG. 8 is a transverse section taken substantially on line 8—8 of FIG. 6.
Figure 7:
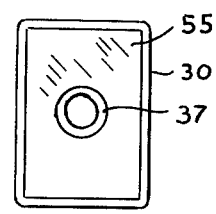
FIG. 7 is a front end view of the device looking in the direction of the arrows 7—7 of FIG. 6.
Figure 10:
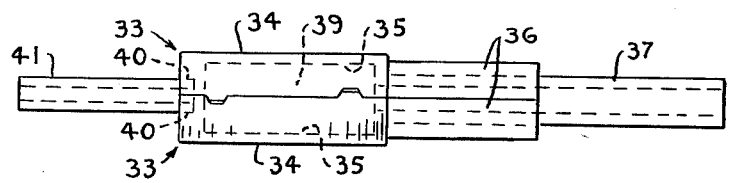
FIG. 10 is a side view of certain of the components or members of the structure shown in FIG. 6.
Figure 11:
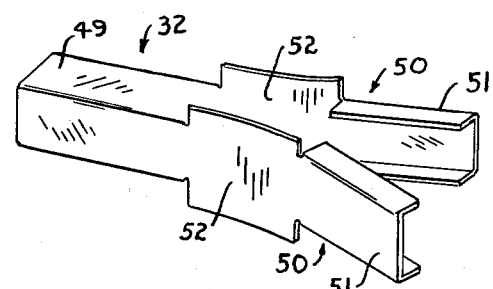
FIG. 11 is a perspective view of an elongated inner casing or holder in which sections forming a mold of the device are mounted.

The device disclosed in FIG. 6 may be designed and constructed in various ways but preferably comprises an outer elongated tubular housing 30 of rectangular cross-section and an assembled structure fixedly secured in the housing. This structure or subassembly includes an elongated inner casing 32 or holder as depicted in FIG. 11 and a pair of relatively thick mating sections generally designated 33, as shown in FIG. 10 which are held in a superimposed relation and mounted in the casing as best shown in FIGS. 6 and 8.

More specifically, each of sections 33 has an enlarged rear extremity 34 provided with a recess 35 and a reduced front channel extension 36. These extensions, in combination, provide a tubular formation which receives an inner extremity of a front tubular means or entrance tube 37 which is preferably constructed of a non-metallic material, such as Pyrex or quartz, and engages an abutment 38 for limiting inward movement of the tubular means. The abutment or wall 38 is notched to provide an opening through which some of the molten material flows into a chamber 39 which is formed by the recesses 35 when the sections 33 are held together in a superimposed relation to constitute a subassembly for disposition in the casing 32. A rear portion of each enlargement 34 of each section is provided with a semi-cylindrical groove 40 and these grooves, in combination, provide a generally cylindrical opening in which a fore end of a rear tubular means or outlet tube 41, also preferably of a non-metallic material, such as quartz or Pyrex is fixedly secured for receiving some of the molten material from the chamber 39 for obtaining a sample in the tube 41, in addition to a larger sample in the chamber, for analysis.

The outlet tube 41 is preferably surrounded by a cylindrical sleeve 42 and a relatively short tubular member 43 is secured in a sleeve 43' in spaced relation to the end of the tube 41 and sleeve 42 to provide a chamber 44 in which a multi-sided movable valve or element 45 is disposed. This valve is responsive to the force of the suction applied to the device and will always allow some air to be evacuated from the device until the valve is automatically rendered inoperative when the chamber 44 has become filled with molten material, which prevents flow into the lance. The sleeve 43' also surrounds the tube 41 and sleeve 42.

An elongated sleeve 46 is disposed about the sleeve 43', and is preferably multi-sided or square in cross-section and of a length which preferably corresponds to that of the sleeve 43' and the length of a rear multi-sided extremity 49 of the casing 32. A relatively short tubular member or sleeve 47, is secured about the inner end of the sleeve 43' and thereby provides a tubular space or socket 48 defined by the outer cylindrical surface of the sleeve 43' the inner surfaces of the multi-sided sleeve 46 and outer end of the sleeve 47. This space or socket serves to detachably accommodate the lower end 20 of the lance 11 which is more or less snugly sealed about the sleeve 43' and against the sleeve 47 so as to substantially prevent leakage of air between the device and lance. The sleeves or members 42, 43, 43', 46 and 47 are preferably constructed of a cellulosic material, such as pasteboard or chipboard, and members 43 and 47 are preferably adhesively secured to member 43' with the inner ends of members 42, 46 and 47 preferably adhesively secured to the enlargements 34 of the half sections 33 in order to protect the outlet tube 41 and impart stability to the structure.

The half sections 33 and outlet tube 41 and sleeves or members about this tube and the entrance tube 37 constitute what may be termed a subassembly which is adapted for disposition in the casing 32, the latter of which will now be described.

The casing 32 as depicted in FIG. 11, is preferably constructed of a cellulosic material, such as pasteboard and includes a rear tubular extremity 49, above referred to, and a pair of relatively movable generally forwardly extending furcations or portions generally designated 50 which are formed by center cutting or splitting upper and lower parallel walls of the casing. The furcations constitute continuations of the side walls of the rear extremity 49 and each furcation includes a front channel extremity 51 and an intermediate relatively wide planar portion 52. The furcations are normally much closer together than shown in FIG. 11 but are shown as being spread apart to initially accommodate the subassembly. The subassembly is adapted to be inserted in between the furcations so that its rear extremity is located in the rear extremity 49 of the casing and the enlargements of the sections will engage the frontal edges of the upper and lower walls of the rear tubular extremity 49 and the furcations are then manually moved inwardly to cause the planar portions 52 to engage the enlargements 34 of the sections 33 and the channel portions 51 to more or less embrace the tubular formation formed by the reduced channels or extensions 36 of the sections whereby the subassembly is retained in the casing 32. If so desired, the sections 33 and/or associated parts may be held assembled by wrapping tape 53 thereabout prior to inserting the subassembly into the casing and after the subassembly has been inserted masses of cement 54 can be placed in the channels 36 and/or thereabout to secure the entrance tube 37 in place and assist in holding the furcations about the formation. Also, if so desired, tape can be wrapped about the channels 51 of the furcations to hold them about the tubular formation formed by the reduced channels of the sections.

In view of the foregoing, it should be manifest that when the device of FIG. 6 is attached to the end 20 of the lance 11, and the entrance tube 37 is inserted into a supply of matter and the vacuum system is correctly operated a vacuum will be created in the lance and thereby induce or cause such material to be expeditiously drawn or sucked successively into the chamber 39 and outlet tube 41 whereby samples are obtained therein for subsequent analysis. The valve 45 allows air to be vacuumed out the outlet tube 41 until it is stopped by metal which flows into the chamber 44 and solidifies to stop the flow.

Figure 12:
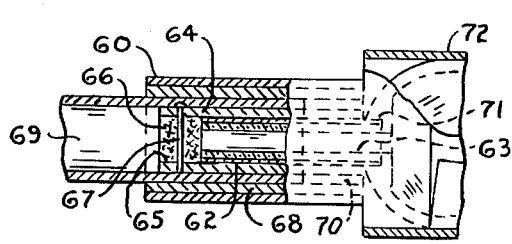
FIG. 12 is a partial vertical section of a rear extremity of internal structure of a modified structure.

Referring to the modified subassembly partially illustrated in FIG. 12, numeral 60 denotes a casing having a rear extremity corresponding to the extremity 49 of the casing 32 in FIG. 11, and a rear structure comprising a tubular member or cylindrical sleeve 62 which is disposed about an outlet tube or tubular means 63 of quartz or some other suitable material. Another cylindrical sleeve or tubular member 64 is secured about the sleeve 62 and extends rearwardly therefrom including the outlet tube 63 to provide a small chamber 65 in which a small mass of steel wool 66 is preferably secured, such as by a crosspin 67. A tubular member or sleeve 68, preferably multi-sided in cross-section, is disposed about the sleeve 64 in a manner whereby the outer cylindrical surface of the sleeve 64 in combination with the internal multi-surfaces of the sleeve 68 define a socket or means for frictionally accommodating the free end of a tubular lance 69 in a manner whereby when the outlet tube is connected to a suction line through the lance 11 and an entrance tube (not shown) of the modified device is inserted into a supply of molten material, some of the latter will be sucked into the chamber of the device, including the outlet tube to obtain a sample having a large portion and a small portion. The mass of steel wool allows air to flow through the device and prevent flow of the material outwardly from the outlet tube. The cross-sectional dimensions of the sleeves 64 and 68 and the lance 69 and their relationship is preferably such that when the lance is inserted into the socket the sides of the sleeve 68 will slightly expand or move radially outwardly and then partially retract and thereby hold the lance in a sealed or substantially fluid tight connection about the sleeve 64 and with respect to the outlet tube 63. A relatively short sleeve or seal or gasket 70 is located about the sleeve 64 is adapted to be engaged by the inner end of the lance 69 so as to substantially provide a complete sealing relationship between the lance and the gasket 70 and thereby provide a unique setup whereby air may be quickly sucked out of the chamber and outlet tube for receiving samples of molten material. The inner end of the outlet tube 63 is preferably fixedly secured by cement in a rear opening formed by grooves 71, (one shown) in the mold sections and the inner ends of the sleeves 62, 64 and 68 are preferably fixedly held against external surfaces of the enlargements of the sections, more or less in the same way that similar sleeves in the subassembly of FIG. 6 are secured. The structure just described may be placed in an outer housing 72 like the housing 30 of FIG. 6.

Figure 13:
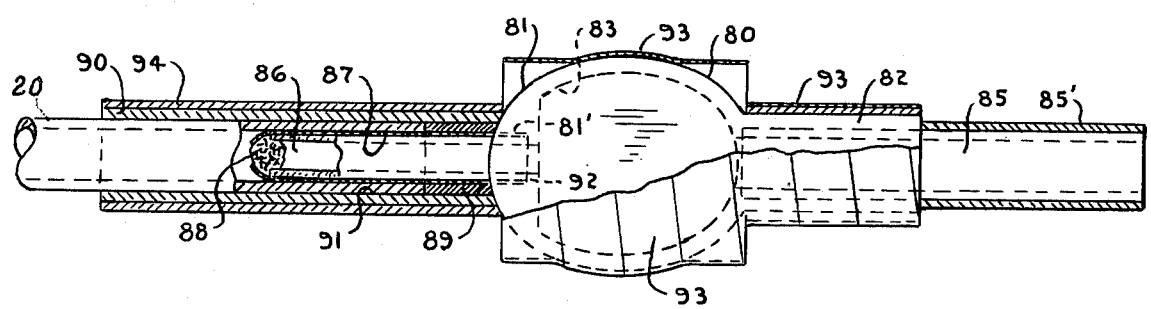
FIG. 13 is a side elevational view of a modified device or structure which is comprised of fewer components or parts than those employed in the structures of FIG. 6.

In FIG. 13 there is depicted a modified structure in which a fewer number of components or parts are utilized. This device preferably comprises a pair of mating sections 80 (one shown) having enlarged rear recessed extremities 81 and reduced front channels or extensions 82 (one shown) which when assembled provide a primary chamber 83 for receiving a sample of molten material and a fore tubular formation in which the rear end of an entrance tube or tubular means 85 is secured. A cylindrical sleeve 85' preferably surrounds the entrance tube for protective purposes. Rear portions of the rear extremities 81 of the sections 80 are respectively provided with mating grooves 81' (one shown) which form an opening in which the fore end of an outlet tube or tubular means 86 is secured for communication with the chamber 83. This outlet tube serves as a secondary chamber for receiving a sample from the primary chamber 83.

The entrance and outlet tubes 85 and 86 are preferably constructed of any material suitable for the purpose, such as quartz or Pyrex, and the outlet tube 86 is preferably protected and supported by a cylindrical sleeve or tubular member 87 which projects a short distance rearwardly of the tube 86 to form a chamber in which a small mass of steel wool 88 is secured and serves substantially the same purpose as the valve 45 and wool 65 as described above. A relatively short sleeve 89, serving as a seal or gasket, surrounds the sleeve 87 and another sleeve 90, multi-sided in cross-section, surrounds the short sleeve 89, sleeve 87 and tube 86. The cross-sectional dimensions of the sleeves, outlet tube and a lance to be used and their relationship are preferably such that the outer marginal end of the short sleeve 89, the outer cylindrical surface of the sleeve 87 and the inner surfaces of the multi-sided sleeve 90 define a socket 91 for accommodating a tubular cylindrical end 20 of a lance, such as 11. It should be observed that the sleeve 90 extends rearwardly an appreciable distance beyond the outer ends of the outlet tube 86 and sleeve 87 thereabout, the purpose of which is to assist in more or less piloting the lance into axial alignment with the outlet tube so that the lance will be correctly received in the socket 91 and thereby locate the outlet tube and sleeve thereabout substantially within the confines of the lance and thereby obtain a substantially fluid tight seal or connection therebetween. The sleeves are preferably constructed of a cellulosic material such as pasteboard or chipboard.

Attention is particularly directed to the fact that the fore end of sleeve 87 surrounds the fore end of the outlet tube and that these fore ends are held in the opening formed by the mating grooves 81' when the sections 80 are assembled. It should be noted that the rear extremities 81 of the mating sections 80 are provided with abutments 92, (one shown) which limit forward movement of the tube 86 and sleeve 87 thereabout. This unique organization is considered to constitute a meritorious advance in the art for the reason that the outlet tube is resiliently supported or mounted and thereby minimizes the possibility of fracturing the outlet tube as well as facilitate a good connection between the lance and device. Otherwise expressed, means are provided for resiliently mounting a tube for use in a device for obtaining a sample of molten material, and irrespective of whether the tube is of an entrance or outlet character.

The mold sections tubes and sleeves are preferably held in a casing or holder more or less corresponding to the casing 32 described above and tape 93 may be wrapped about the casing as shown to provide a composite structure or assembly. It should be noted that the casing is provided with a relatively long or extended rear extremity 94 in which the rear tube 86 and sleeves 87, 89 and 90 are confined.

Figure 14:
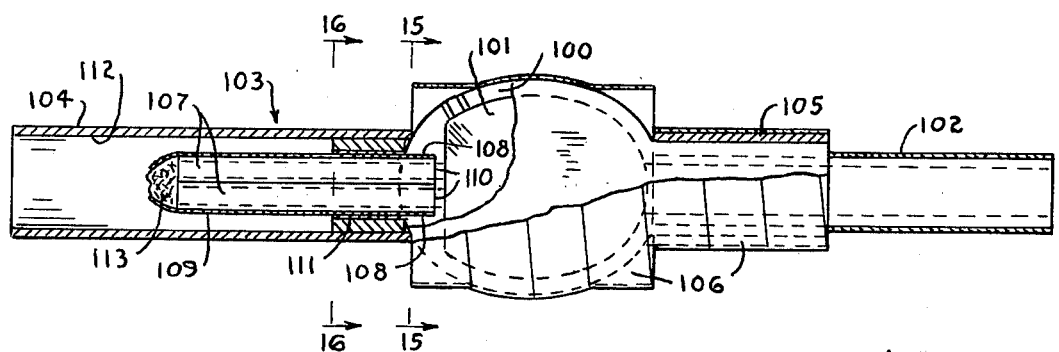
FIG. 14 is a side elevational view of a modified device illustrating a pair of tubular means which are resiliently supported in a unique manner.
Figure 15:
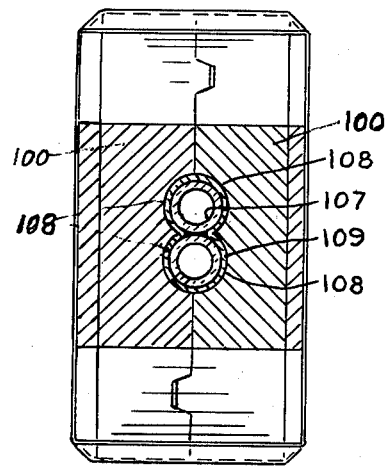
FIG. 15 is an enlarged transverse section taken substantially on line 15—15 of FIG. 14.
Figure 16:
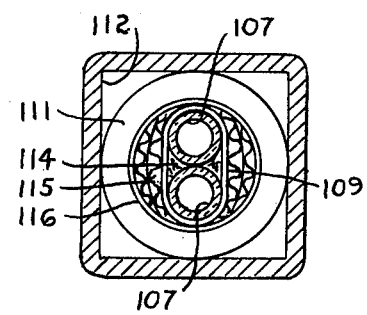
FIG. 16 is an enlarged transverse section taken substantially on line 16—16 of FIG. 14 illustrating details of construction.

Referring to the modification illustrated in FIGS. 14, 15 and 16, there is disclosed a device comprising, among other things, wall structure comprising a pair of mating sections 100 formed to provide enlarged recessed rear extremities providing a chamber 101 and a reduced tubular front formation in which an entrance tube 102 is secured. These sections are secured in an elongated casing or holder generally designated 103 which substantially corresponds to the casing shown in FIGS. 11 and 13. More specifically, the casing shown in FIG. 14 includes a relatively long rear extremity 104 and a shorter front extremity 105. Tape 106 may be utilized to hold the furcations of the casing about the mating sections and the latter assembled.

The device shown in FIGS. 14, 15 and 16 primarily differs from the device of FIG. 13 by providing the device with a pair of associated outlet tubes 107; eliminating certain of the components of FIG. 13, and providing a setup whereby the rear extremity 104 of the casing or holder 103, at least serves the dual purpose of protecting the rear tubes and affording a socket for an end of a lance.

More particularly, each of the mating sections is provided with a pair of parallel substantially semi-cylindrical grooves 108 which form a pair of cylindrical openings which receive the fore ends of the tubes 107 and the fore end of a sleeve 109 surrounding the tubes. The sections are also provided with abutments 110 at the inner ends of the grooves or openings whereby to limit entry of the tubes and sleeve into the openings and thereby correctly locate or position them in relation to one another and the sections.

A relatively short sleeve 111 constituting a seal or gasket is disposed in the extremity 104 and about the tubes 107 and sleeve 109 and this sleeve in combination with the multi-sided rear extremity 104 of the casing defines an elongated socket 112 which accommodates the tubular end of a lance in a manner to receive the tubes and provide a sealed connection between the lance and device, the purpose of which is obvious in view of what has been described above with respect to the other devices.

As illustrated in FIG. 15, the sleeve 109 is clamped about the tubes 107 and as depicted in FIG. 14, the sleeve extends rearwardly a short distance beyond the tubes and is curved or turned inwardly to provide a chamber in which a mass of steel wool 113 or other suitable material is confined whereby to permit the flow of air through the device but prevent the flow of metal outwardly from the tubes 107.

In order to reenforce or impart greater stability to the tubes 107 and sleeve 109, an inner mass of filler material such as 114 is disposed longitudinally between portions of the tubes within the confines of the sleeve 109 and outer portions about the sleeve as indicated at 115 in FIG. 16. An additional sleeve 116 surrounds the outer filler material 115 and sleeve 109 to provide a substantially cylindrical formation which is adapted to be more or less snugly received in the tubular end of a lance when the latter is inserted into the rear extremity 104 of the casing or holder 103. Due to the multi-sided character of the extremity 104 and cross-sectional dimensions of the lance, it is intended that the walls or sides of the rear extremity will slightly expand when the lance is inserted into the socket and guide the lance inwardly and about the formation so as to establish a sealed connection between the lance and device when the end of the lance engages the seal or gasket 111.

It is to be understood that in all of the devices described above the sockets are preferably of such a character that at least portions thereof may expand and contract to some extent when a lance is being attached to a device but this factor is not absolutely essential.

Figure 17:
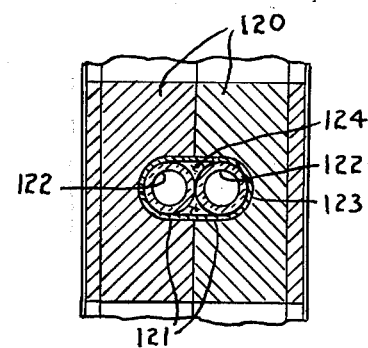
FIG. 17 is partial sectional view showing a different arrangement of a pair of outlet tubes respectively mounted in a pair of mating sections.

In FIG. 17 there is depicted a partial section similar to FIG. 15 which shows a setup whereby each of a pair of mating mold sections 120 is provided a relatively deep groove 121 which receives an outlet tube 122, including a portion of a sleeve 123. The sleeve surrounds the tubes 122 and serves to resiliently support the tubes in an opening formed by the grooves 121 when the sections 120 are correctly assembled. Filler material 124 is preferably placed between portions of the tubes and additional filler material about the sleeve 123 and an additional sleeve about the additional filler material more or less in accordance with the disclosure in FIG. 16 to provide a cylindrical formation for reception in a lance.

Having thus described my invention or inventions, it is obvious that various modifications or additions to those described may be made in the same without departing from the spirit of the invention and, therefore, I do not wish to be understood as limiting myself to the exact forms, constructions, arrangements, and combinations of the components herein shown and described.

I claim:

1. Structure for the purpose described comprising a pair of pipes, a coupling communicatively connecting said pipes together in an angular relationship, said coupling having a chamber and an outlet, one of said pipes having an extremity provided with means for supporting a device for receiving a sample of molten material from a supply thereof, and the other of said pipes having an end for connection with a source of air under pressure for causing the air to flow through said chamber and outlet in a manner whereby to cause air to be evacuated from said one pipe and thereby induce the flow of such a material into such a device.

2. The structure defined in claim 1, including a manually operable valve for controlling the flow of air through said pipes, coupling and outlet.

3. The structure defined in claim 1, including means disposed in said chamber for increasing the velocity of the air through the outlet.

4. The structure defined in claim 1, including means attachable to said other pipe within the confines of said chamber for jetting the air through the outlet.

5. The structure defined in claim 1, in which said coupling is in the form of a T, said other pipe is connected to said T, an additional pipe is connected to said T in axial alignment with said other pipe to constitute an extension of said outlet, and said one pipe is connected to said T at an angle with reference to said aligned pipes.

6. The structure defined in claim 1, including a plurality of different elements any one of which may be selectively disposed in the chamber for jetting the air through the outlet.

7. The structure defined in claim 1, in which said extremity for supporting such a device can be manually adjusted with respect to the remainder of the pipe whereby to facilitate positioning of the device in a supply of such a material.

8. A lance for the purpose described, said lance comprising an inner extremity which serves as a handle for manipulating the lance, an outer extremity which serves to support a device for obtaining a sample of molten material from a supply thereof, and means operatively connecting said extremities whereby these extremities may be manually adjusted with respect to one another in any one of an infinite number of positions.

9. The lance defined in claim 1, in which said connecting means is of a flexible character.

10. The lance defined in claim 1, in which said lance is tubular and its inner extremity is somewhat longer than its outer extremity.

11. An assembly of the kind described comprising a pair of elongated tubular members, means for connecting one of said members to an air pressure structure, the other of said members having a free end for supporting a device for obtaining a sample of molten material from a supply thereof, and means operatively connecting said members for manual relative angular movement whereby to facilitate locating such a device for entry into such a supply.

12. A device for obtaining a sample of molten material from a supply thereof, said device comprising wall structure forming a chamber, front tubular means communicatively connected to said chamber, rear tubular means communicatively connected to said chamber, a plurality of tubular members telescopically connected together and about said rear tubular means and providing a socket for detachably accommodating a free end of a tubular lance in a manner whereby when said front tubular means is inserted into a supply of material and air is evacuated from said lance some of the material will be induced to flow into said chamber for eventual solidification therein.

13. A subassembly of a device for obtaining a sample of molten material from a supply thereof, said subassembly comprising wall structure forming a chamber, a rear opening and a front tubular formation, a front tubular entrance secured in said tubular formation for receiving such a material for flow into said chamber, and a rear tubular means secured in said opening for communication with said chamber and having a rear extremity for reception in a tubular end of a lance.

14. The subassembly defined in claim 13, including a pair of sleeves surrounding said rear tubular means defining a socket for receiving a tubular free end of a lance in a manner whereby when the front entrance is inserted into such a material and air is evacuated from such a free end the material will be sucked into said chamber and said rear tubular means.

15. The subassembly defined in claim 13, including a cylindrical sleeve surrounding said rear tubular means, a multi-sided outer expansible-contractible sleeve surrounding said cylindrical sleeve and defining in combination therewith a socket whereby said outer sleeve will expand and partially contract when a tubular free end of a lance is inserted into the socket.

16. The subassembly defined in claim 13, including an elongated tubular casing in which said subassembly is substantially disposed, and said casing has a rear extremity which surrounds said rear tubular means and extends a predetermined distance therebeyond.

17. A subassembly of a device for obtaining a sample of molten material from a supply therof, said subassembly comprising wall structure forming a primary chamber, a rear opening and a front tubular formation, a rear tubular means secured in said opening and having a rear extension and a front tubular entrance secured in said tubular formation for receiving such a material for flow into said rear tubular means via said chamber, and means surrounding said rear extension providing a socket for accommodating a free end of a lance whereby said extension is received therein.

18. A subassembly of a device for use in obtaining a sample of molten material from a supply thereof, said subassembly comprising wall structure forming a chamber, a front tubular formation and a rear opening, a rear outlet tube secured in said opening and communicating with said chamber and an entrance tube secured in said formation for receiving such a material for flow into said chamber and outlet tube, a pair of sleeves surrounding said outlet tube defining a socket about the latter for accommodating a tubular lance connectible with means for evacuating air from the device whereby to induce the flow of such a material into the device when the entrance tube is inserted into such material.

19. A device for obtaining a sample of molten material from a supply thereof, said device comprising an elongated casing, wall structure mounted in said casing and forming a chamber, a front tubular formation and a rear opening, a rear outlet tube secured in said opening and communicating with said chamber and an entrance tube secured in said formation for receiving such a material for flow into said chamber and outlet tube, means surrounding said outlet tube defining a socket about the latter for accommodating a tubular lance connectible with means for evacuating air from the device whereby to induce the flow of such a material into the device when the entrance tube is inserted into such a material.

20. In combination: wall structure forming a chamber and a front entrance for receiving molten material for flow into said chamber, said wall structure also forming a rear opening, tubular means secured in said opening for receiving some of such material from said chamber, and a gasket sleeve surrounding said tubular means for limiting inward movement of a tubular end of a lance when said tubular means is received in said lance end.

21. A subassembly for attachment to wall structure having a chamber, a front entrance for receiving molten material for flow into the chamber and also having a rear outlet opening, an elongated rear tube secured in said opening for receiving such a material from said chamber, and a gasket surrounding said tube for limiting inward movement of a tubular end of a lance when said tube is received in said end.

22. A subassembly of a device for obtaining a sample of molten material from a supply thereof, said subassembly comprising a chamber having a front entrance for receiving the material for flow into said chamber and a rear non-metallic tube communicatively connected to said chamber for receiving such a material therefrom, and a gasket disposed at least about one end of the tube for limiting inward movement of a tubular end of a lance when said tube is received in said end.

23. A subassembly comprising wall structure forming a chamber having a front entrance for receiving a sample of molten material from a supply thereof for flow into the chamber and also forming a rear opening, rear tube, means supporting one end of said tube in said opening to place said tube in communication with said chamber, and a gasket surrounding said tube for limiting inward movement of a tubular end of a lance about said tube.

24. The subassembly defined in claim 24, in which an additional rear tube is supported in said rear opening to place this tube in communication with the chamber.

25. A subassembly of a device for obtaining a sample of molten material from a supply thereof, said subassembly comprising a pair of tubes, means securing said tubes in a side-by-side relation, means secured about at least portions of said tubes whereby to provide a substantially cylindrical formation for reception in a tubular end of a lance, and an annular gasket surrounding an inner area of said formation for limiting the extent of its reception in said lance end.

26. A subassembly of a device for obtaining a sample of molten material from a supply thereof, said subassembly comprising an elongated casing, wall structure mounted in said casing and provided with a chamber and a front entrance for receiving such a material for flow into said chamber, said wall structure also being provided with an opening and said casing having a multi-sided rear tubular extremity, tubular means resiliently mounted on said wall structure for communication with said chamber and extending rearwardly into said rear extremity, and means disposed in relation to said tubular means for engagement by a tubular end of a lance in a manner whereby when the front entrance is inserted into a supply of such a material and air is evacuated from the lance, such a material will be drawn into said chamber and tubular means.

27. A device for obtaining a sample of molten material from a supply thereof, said device comprising an elongated casing having a rear tubular extremity, an intermediate area and a front extremity, wall structures having a chambered enlargement disposed in said intermediate area and a tubular formation supported by said front extremity, an entrance tube secured in said tubular formation for receiving a sample of such a material for flow into said enlargement, said wall structure also having an opening, tubular means having a fore end secured in said opening for communication with the enlargement and a rear extremity extending rearwardly into the rear extremity of said casing, a gasket disposed in said rear extremity about said tubular means, and said gasket and the interior of said rear extremity defining a socket for detachably receiving a tubular end of lance in a manner whereby when the entrance tube is inserted into a supply of such a material and air is evacuated from the lance some of such material will be sucked into the chambered enlargement and tubular means to obtain samples for subsequent analysis.

* * * * *